United States Patent [19]

Martin et al.

[11] Patent Number: 4,791,098

[45] Date of Patent: Dec. 13, 1988

[54] 2-METHYL-3-(P-METHYLPHENYL)PROPIONITRILE, PREPARATION AND USE THEREOF AS SCENT

[75] Inventors: Roland Martin, Kallstadt; Walter Gramlich, Edingen-Neckarhausen, both of Fed. Rep. of Germany

[73] Assignee: BASF Aktiengesellschaft, Rheinland-Pfalz, Fed. Rep. of Germany

[21] Appl. No.: 119,539

[22] Filed: Nov. 12, 1987

[30] Foreign Application Priority Data

Nov. 15, 1986 [DE] Fed. Rep. of Germany ....... 3639158

[51] Int. Cl.$^4$ ................................................ A61K 7/46
[52] U.S. Cl. ........................................ 512/20; 558/388
[58] Field of Search .................. 512/20; 558/388, 400

[56] References Cited

FOREIGN PATENT DOCUMENTS 0062368 10/1982 European Pat. Off. ............ 558/388
1130265 6/1986 Japan ................................... 558/388

OTHER PUBLICATIONS

Research Disclosure 22501 (Jan. 1983).
Chemical Abstract, vol. 80 (1974), 108,143q.
Chemical Abstract, vol. 78 (1973), 84,009f.

*Primary Examiner*—Werren B. Lone
*Attorney, Agent, or Firm*—Oblon, Fisher, Spivak, McClelland & Maier

[57] ABSTRACT

2-methyl-3-(p-methylphenyl)-propionitrile is prepared for use as a scent.

3 Claims, No Drawings

2-METHYL-3-(P-METHYLPHENYL)PROPIONITRILE, PREPARATION AND USE THEREOF AS SCENT

In the field of perfumery and aroma development there continues to be, despite the large number of existing natural and synthetic scents, a substantial demand for new scents which either have previously unknown notes or, however, can replace costly and/or comparatively inaccessible scents. The reason is the evergrowing demand for scent compositions not only for fine perfumery but also for cosmetic and industrial products such as washing agents, fabric softeners and the like.

Compounds which have a pure jasmine scent are much in demand since the supply of natural jasmine base is limited. Many attempts have therefore been made to synthesize the jasmine ingredients (cf. E. P. Demole, The Fragrance of Jasmine in Fragrance Chemistry, editor E. T. Theimes, Academic Press 1982, pages 362–396). However, these naturally occurring materials are not easy to synthesize.

There have been disclosed totally synthetic compounds having a jasminelike note which, structurally, have nothing in common with natural jasmine ingredients (cf. loc. cit. pages 387–90). Specific examples are 2-benzylideneheptanal, 2-benzylideneoctanal, 2-furfurylideneheptanal, ethyl 2-acetyloctanoate, tetrahydropyran-4-yl acetate and 1,3-dioxanes having a linear $C_5$–$C_7$ sidechain. A disadvantage of existing jasmine scents is either that the jasmine scent is not pure (ethyl 2-acetyloctanoate) or that the tenacity and/or the chemical stability leave something to be desired (benzylideneoctanal and benzylideneheptanal).

It is an object of the present invention to synthesize a compound which is easily accessible, has a tenacious pure jasmine scent and has substantial stability in various application areas.

We have found that this object is achieved, surprisingly, by the novel 2-methyl-3-(p-methylphenyl)propionitrile of the formula I

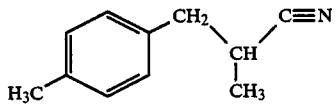
(I)

which is a compound having a particularly pure jasmine scent which, furthermore, is extremely stable within a wide pH range. A further particular advantage of the novel jasmine scent I is its remarkably high tenacity (about 7 days according to tests with scent strips).

The present invention accordingly provides not only the novel compound I but also a method of using it as a scent and also a scent composition containing this compound I.

I is a novel compound. It is true that some compounds of similar structure are described in the literature but only as intermediates for synthesizing other compounds.

For instance, 2-methyl-3-(p-tert.-butylphenyl)-propionitrile (CAS No. 93,981-807) is known from Research Disclosure 225-001 (January 1983) as an intermediate for preparing 2-methyl-3-(p-tert.-butyl)propionaldehyde. 2-Methyl-3-(p-isopropylphenyl)propionitrile (CAS No. 67,845-51-6) is also known.

Furthermore, 2-methyl-3-(p-methoxyphenyl)propionitrile is known from C.A. 80 (1974), 108, 143q and C.A. 78 (1973), 84009f as an intermediate for preparing 2-methyl-3-(p-methoxyphenyl)ethylamine.

As our own studies have shown, this nitrile has has a floral, fruity scent which, however, is weaker than than that of the corresponding aldehyde which is commercially available as a scent under the trade name Canthoxale ®.

The scent I according to the invention is prepared in a conventional manner, for example by reacting 2-methyl-3-(p-methylphenyl)propanal with hydroxylamine and dehydrating the resulting oxime with acetic anhydride (cf. R. DeSimone, Nitriles in Perfumery, in Perfumer & Flavorist -4 (1980), 1–8, in particular 6). 2-Methyl-3-(p-methylphenyl)propanal itself is a readily available scent having a strong orange fragrance and a slight jasmine note. It is surprising that on converting the aldehyde into the corresponding nitrile the dominant orange fragrance disappears completely and a strong and very pure jasmine scent is obtained.

This is all the more true since in loc. cit. it is stated on page 7, left-hand column, that nitriles very frequently haveodors analogous to the corresponding aldehydes or were observed to be virtually odorless and that there exists no proper explanation for large differences in the scent between aldehydes and nitriles.

A particular advantage of compound I, used as a scent according to the invention, is in addition to the pure jasmine scent the high tenacity (~7 days) and the high chemical stability, in particular in the basic range (pH 14), so that the compound according to the invention is usable not only in fine perfumery but also more widely in soaps and washing and cleaning agents.

Compound I according to the invention is excellently combinable with conventional perfume ingredients and other scents to give novel compositions upon which said compound I likewise confers a high tenacity. The proportion of I in the scent compositions is in general 1–50 percent by weight. Compositions of this kind can be used for perfuming cosmetic formulations such as creams, lotions, toilet waters, aerosols, toilet soaps and mouth care agents and also in "extrait" perfumery; they can further be used for improving the odor of industrial products such as fabric softeners and washing and cleaning agents.

EXAMPLE

In a flask, 93 g (1.34 mol) of hydroxylammonium chloride were dissolved in 170 ml of water. 267 g of 20% strength sodium hydroxide solution were added dropwise. After addition was complete, the solution was stirred for 10 minutes (min), and 162 g (1 mol) of 2-methyl-3-(p-methylphenyl)propanal were then added dropwise. The reaction mixture was then stirred at room temperature for 12 hours (h), 400 ml of toluene were then added, and the mixture was stirred for a further 30 min. The organic phase was separated off, washed twice with 150 ml of water each time, and dried and evaporated.

The crude oxime was added dropwise at 100° C. to 680 g (6.66 mol) of acetic anhydride in the course of 1 h. This was followed by refluxing for 3 h, cooling to 80° C. and hydrolysis with 330 ml of water in the course of 3–4 h. The mixture was cooled down with stirring to room temperature and extracted three times with 250 ml of toluene each time. The organic phases were combined and washed neutral by washing twice with 150 ml of water each time and once with 100 ml of 10% strength sodium hydroxide solution, evaporated and distilled to give 126 g (corresponding to 79% of theory) of 2-methyl-3-(p-methylphenyl)propionitrile of boiling point=77°–93° C./0.4 mbar $d^4 = 0.9588$ g/cm$^3$; $n_D^{20} = 1.5100$ MS:M$^+$ =159 (8%), 105 (100%), 77 (10%) m/e IR (film):=ν(C≡N) 2259, 1516, 1455, 819, 792, 753 cm$^{-1}$ $^1$H-NMR(CDCl$_3$): δ=1.25 (d, 3H), 2.3 (s, 3H), 2.75 (m, 3H), 7.1 (m, 4H) ppm $^{13}$C-NMR(CDC13): δ=17.5 (Q), 20.9 (Q), 27.48 (d), 39.47 (t), 122.55 (S), 128.9 (d), 129.8 (d), 133.9 (S), 136.6 (S) ppm Fragrance note: a fine, pure jasmine scent The jasmine scent was still readily perceptible 7 days after application to scent paper.

We claim:

1. 2-Methyl-3-(p-methylphenyl)propionitrile.

2. A scent composition containing 2-methyl-3-(p-methylphenyl)propionitrile.

3. A scent composition as claimed in claim 2 containing 2-methyl-3-(p-methylphenyl)propionitrile in an amount of from 1 to 50 percent by weight, based on the total composition.

* * * * *